United States Patent [19]

Locher

[11] 4,196,627

[45] Apr. 8, 1980

[54] METHOD AND APPARATUS FOR OBTAINING A SELECTIVE LIQUID SAMPLE FROM NEAR THE BOTTOM SURFACE OF A LIQUID-FILLED TANK

[75] Inventor: J. Hartley Locher, Norwalk, Conn.

[73] Assignee: Mobil Oil Corporation, New York, N.Y.

[21] Appl. No.: 937,293

[22] Filed: Aug. 28, 1978

[51] Int. Cl.² ........................ G01N 1/10; G01N 1/14
[52] U.S. Cl. .............. 73/425.6; 33/126.4 R; 73/425.4 R
[58] Field of Search ......... 73/425.4 R, 425.6, 425.4 P; 33/126.4 R; 361/215

[56] References Cited

U.S. PATENT DOCUMENTS

| | | | |
|---|---|---|---|
| 1,511,591 | 10/1924 | Colligan | 73/425.4 R |
| 1,705,121 | 3/1929 | Jones | 33/126.4 R |
| 2,593,830 | 4/1952 | Baker | 73/425.4 R |
| 3,062,056 | 11/1962 | Wicoff | 73/425.6 |
| 3,129,513 | 4/1964 | Porter | 73/425.4 R |
| 3,555,170 | 1/1971 | Petzetakis | 361/215 |

FOREIGN PATENT DOCUMENTS 651374  3/1951  United Kingdom ............... 73/425.4 P Primary Examiner—S. Clement Swisher
Assistant Examiner—Denis E. Corr
Attorney, Agent, or Firm—C. A. Huggett; Drude Faulconer

[57] ABSTRACT

A method and apparatus for obtaining a sample of liquid, e.g. water, from near the bottom of a liquid-filled container, e.g. a crude or other refined oil-filled cargo tank. The method utilizes a sampling apparatus comprising a conduit, closable at its upper end, which is attached to a water-sounding bob to be lowered therewith. When the bob is on the bottom of the tank, and the conduit is thus positioned as desired above the bottom, the conduit is opened to permit the liquid at the depth being sampled to flow upward in the conduit to a level approximately equal to the liquid level in the tank. A suction is then applied to the upper end of the conduit to recover this bottom sample. The conduit is normally stored on a reel which is also used to raise and lower the conduit and a hand-held pump is used to apply the suction. This makes the apparatus portable, totally self-contained and readily available when needed.

14 Claims, 11 Drawing Figures

U.S. Patent  Apr. 8, 1980  Sheet 1 of 2  4,196,627
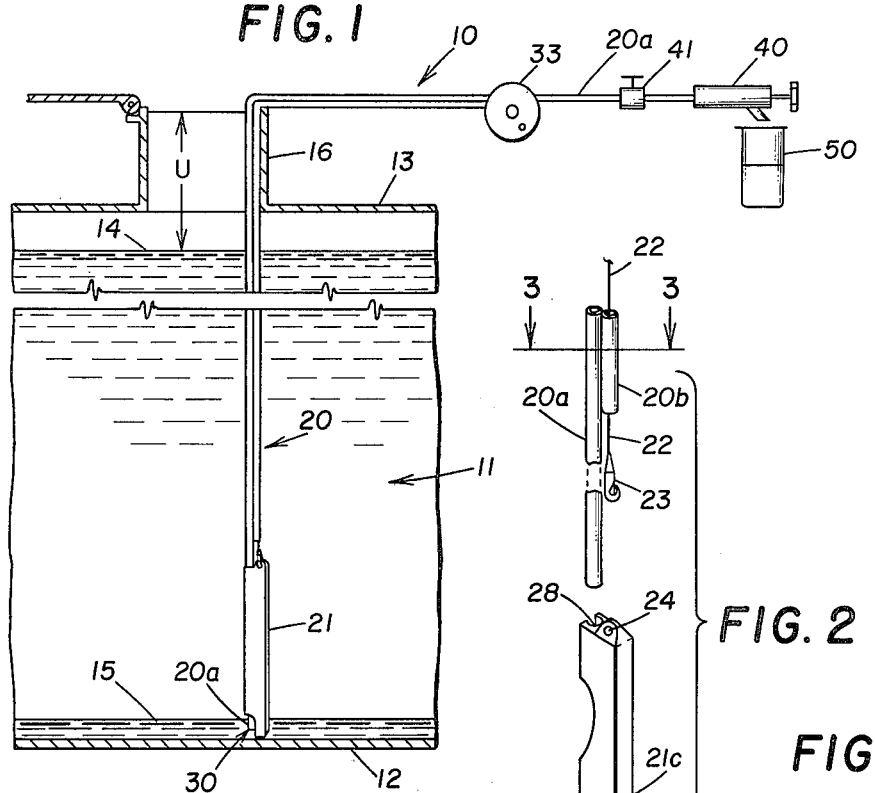
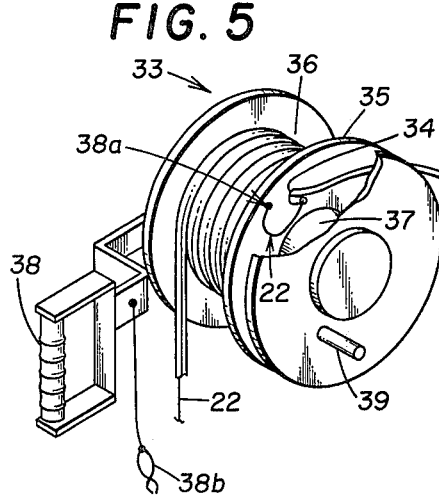
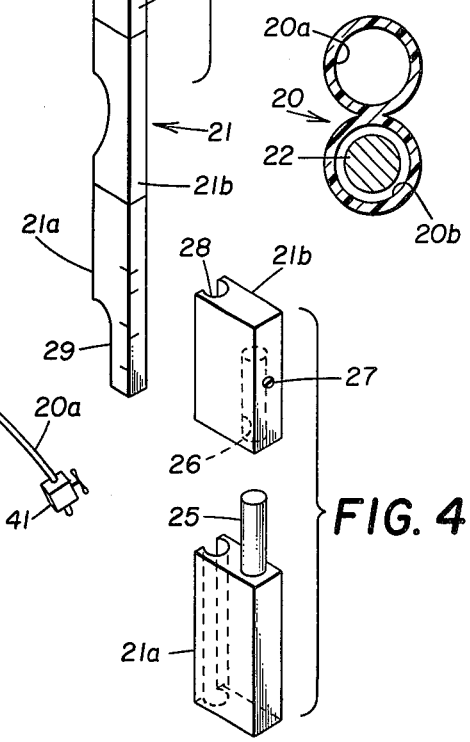

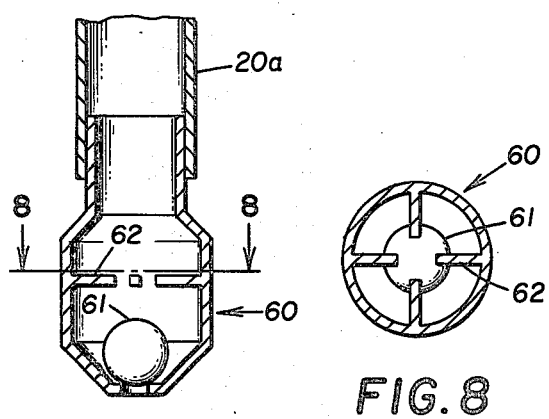
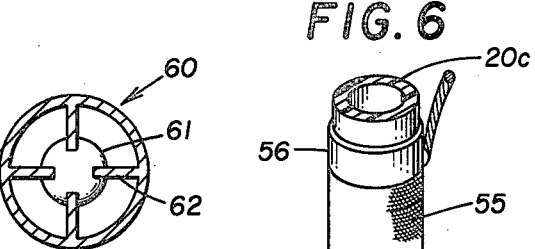
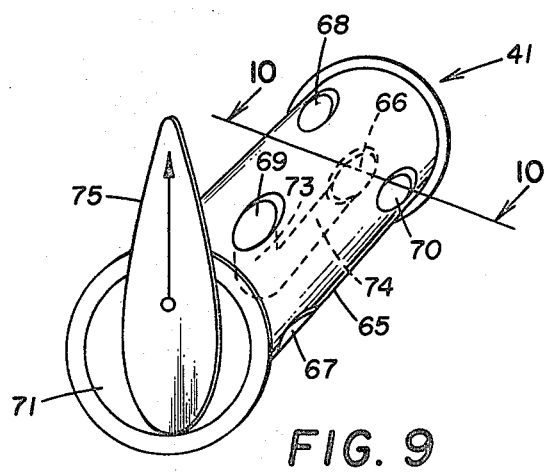
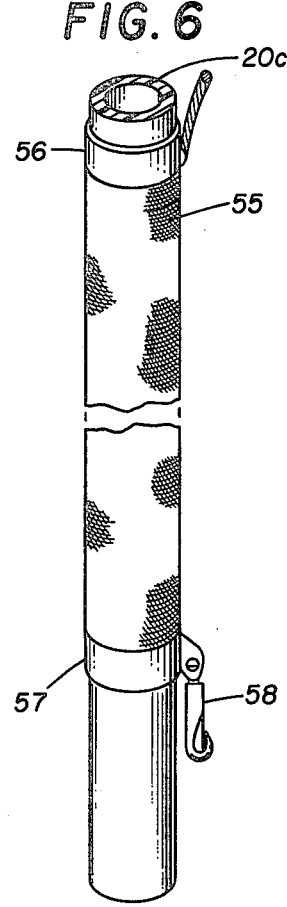
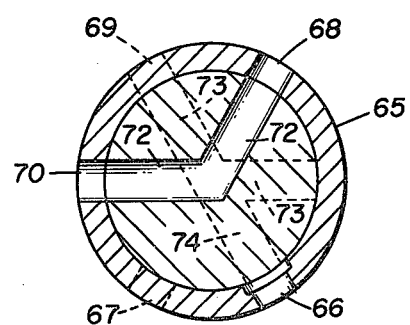

METHOD AND APPARATUS FOR OBTAINING A SELECTIVE LIQUID SAMPLE FROM NEAR THE BOTTOM SURFACE OF A LIQUID-FILLED TANK

BACKGROUND OF THE INVENTION

The present invention relates to a method and apparatus for obtaining a sample of liquid from near the bottom of a liquid-filled container and more particularly relates to a method and apparatus for obtaining a sample from a layer of water or water-oil emulsion underlying crude oil in a cargo tank.

In many instances, cargo oil, e.g. crude or refined oil which is loaded onto tanker ships is contaminated with substantial amounts of water. It can be easily understood that if payment for the purchased oils is based on the measured volume of total liquid in the cargo tanks, the final cost to a buyer may be substantially inflated since he pays for the useless water at cargo oil prices. In many actual cargo oil purchasing situations existing today, the buyer is allowed to deduct the volume of water in the cargo tanks only if he can prove that it was pumped aboard with the cargo oil and was not already present in the tanks before the cargo oil was loaded.

Since water inadvertently left in the tanks (e.g. seawater used for ballast, etc.), will have a substantially different composition from the water loaded with the cargo oil (e.g. formation water produced with the crude or condensate from steam used in processing the produced oil, etc.), the origin of the water in question can readily be established if a sample of the water can be obtained from a cargo tank for analysis after it has been loaded.

Further, by knowing the origin of any water in a loaded cargo tank, steps can be taken to alleviate the contamination problem. That is, if the water is being pumped in with the cargo oil, further processing of the cargo oil can be undertaken to remove the water before loading or if the water is originally present in the tank, further steps can be taken aboard the ship to remove such water before loading. Therefore, it can readily be seen that an important need exists for obtaining a sample of any water or water-oil emulsion that may be present in a cargo tank after it has otherwise been loaded with crude or refined oil.

SUMMARY OF THE INVENTION

The present invention provides a simple, fast, and reliable method and self-contained apparatus for obtaining a sample of liquid, e.g. water, from near the bottom of a liquid-filled container, e.g. a crude or refined oil-filled cargo tank aboard a tanker ship. The sampling method utilizes an inexpensive apparatus which is self-contained, portable, easily storable and requires no external power source aboard ship thereby providing immediate sampling capabilities for any environment, e.g. crude tankers, where such are needed.

More specifically, the present method utilizes a sampling apparatus comprising a conduit which is attached to a weight such as a "water-sounding bob" and is lowered therewith through cargo oil or other overlying liquid into the liquid to be sampled. Preferably, the conduit is constructed from a clear, flexible, thick-walled plastic material formed in a siamese tube configuration to provide two separate passages throughout its length. The flexible, electrically conductive metal line which is attached to the bob for lowering and raising same is passed through one of the passages while the other passage provides the liquid passage through which the sample is recovered. The first passage provides support around the electrically conductive grounding line during operation which is an important consideration in those environments where the possibility of an explosion exists. The liquid or sample passage is closable at its upper end by means of a valve or the like and is closed while the conduit is lowered into the tank thereby preventing any substantial amount of liquid, e.g. crude or other oil overlying the water layer from rising in the sample passage until the lower end of the conduit is in position.

When the bob reaches a desired depth, usually standing on the bottom of the tank, the end of the sample passage is precisely positioned at a point within the liquid layer to be sampled. The valve at the top of the sample passage is then opened and the head of cargo liquid in the tank causes the liquid adjacent the lower end of the sample passage to rise in the sample passage to a level approximately equal to the surface level of the cargo liquid. Suction is then applied at the upper end of the sample passage preferably by means of a hand-held pump to finish recovering the sample.

The sample conduit is normally stored on a portable reel which is also used to lower and raise the conduit and bob in the tank. Further, the bob is preferably made in sections so it can be easily disassembled for storage. Still further, a means is provided for easily purging the sample passage when an operation has been completed.

In many situations, if a small amount of crude or other cargo oil rises in the sample conduit while it is being lowered, it will not present any problems to the sampling operation. This oil will merely rise ahead of the water sample and is easily separated from the recovered sample. However, where the cargo oil is one having a low vapor pressure and/or where the loading temperatures are high, any oil in the sample passage may flash or vaporize as it rises in the sample passage thereby preventing severe vapor lock problems for the suction means. In the latter mentioned situations, another embodiment of the present invention includes an upward opening check valve affixed in the lower end of the sample passage. The sample passage in this other embodiment is filled with a nonvolatile immiscible liquid or distilled water and the valve at the top of the sample passage is closed. The nonvolatile liquid or distilled water in the sample passage will keep the check valve closed while the sample conduit is lowered into position while the check valve prevents any cargo oil from entering the sample passage. When the conduit is in position, the valve at the top of the sample passage is opened and the suction means is actuated. As the nonvolatile liquid or distilled water is withdrawn, the check valve will open and the desired sample will flow up the sample passage behind the immiscible liquid for recovery.

BRIEF DESCRIPTION OF THE DRAWINGS

The actual construction, operation, and the apparent advantages of the present invention will be better understood by referring to the drawings in which like numerals identify like parts and in which:

FIG. 1 is a partial vertical sectional view of the present invention in an operable position within a crude oil cargo tank;

FIG. 2 is an exploded perspective view of the water-sounding bob and the lower end of the sampling conduit;

FIG. 3 is a cross-sectional view taken along line 3—3 of FIG. 2;

FIG. 4 is a perspective view, partly broken away, of a joint used to couple the sections of the water-sounding bob;

FIG. 5 is a perspective view partly broken away, of a reel mechanism used to raise and lower the sampling conduit;

FIG. 6 is a perspective view of another embodiment of the present invention;

FIG. 7 is a vertical sectional view of the lower portion of a second embodiment of the present invention;

FIG. 8 is a sectional view taken along line 8—8 of FIG. 7;

FIG. 9 is a perspective view of a valve used in the present invention;

FIG. 10 is a sectional view taken along line 10—10 of FIG. 9 showing the valve in a first position; and FIG. 11 is a sectional view taken along line 10—10 of FIG. 9 showing the valve in a second position.

DESCRIPTION OF THE PREFERRED EMBODIMENT

When water contaminated cargo oil such as crude or refined oil is loaded into a cargo tank of a tanker ship, the water will gravitate to the bottom of the tank to form a layer of water and/or water-oil emulsion underlying the cargo oil. This water may be part of that originally produced with the crude or may have become entrained in the cargo oil during processing, e.g. steam condensate, desalting, water-washing, etc.

When a cargo tank is filled to a desired level or volume, the ullage (i.e., the distance from a specified hatch to the top surface of the cargo oil) is measured and the total volume of liquid which may be water contaminated in the tank is determined from a set of standard ullage tables for the particular cargo tank being loaded. Next, a brass water-sounding bob is lowered on a line to the bottom of the cargo tank to discover and/or measure the depth of any water layer which has formed in the tank. As understood by those skilled in the art, the bob is coated with a substance which is unaffected by oil but which will change color when contacted by water. By observing the level of color change on the bob to indicate either presence or depth, the volume of contaminating water or water-oil emulsion in the loaded tank can easily be computed.

However, in some instances the contaminating water layer in the cargo tank may not originate from the produced cargo oil but may, instead, result from water inadvertently left in the tank after it has been substantially emptied of ballast water or the like. As explained above, establishing the source of any water layer underlying the cargo oil is of vital importance in determining final payment due for the net cargo oil and/or for taking corrective methods to reduce the amount of water in the tank in future loadings.

Referring more particularly to the drawings, FIG. 1 discloses sampling apparatus 10 in an operable position within cargo tank 11 of a tanker ship or the like. Tank 11 has a bottom 12 and a top normally formed by deck 13 and is shown substantially filled with cargo oil 14 which has an underlying layer 15 of water and/or water-oil emulsion therein. Hatch 16 on deck 13 provides entry into tank 11.

Sampling apparatus 10 is comprised of conduit 20 which is attached to water-sounding bob 21 and is lowered therewith on line 22 from hand-held reel 33 to a position on the bottom 12 of tank 11. In the preferred modification, conduit 20 is comprised of small, soft, thick-walled, clear plastic siamese tubing (e.g. Estane, Bevilon, poly-butylene, Tygon, or the like) having a siamese or figure-8 cross section (see FIG. 3) which forms two separate passages 20a and 20b. Passage 20a provides the passage through which a liquid sample is taken from within the water layer 15 on the bottom of tank 11. Passage 20a is sized small, e.g. ¼ inch internal diameter to minimize flotation tendencies and to minimize purging from passage 20a, when needed. The wall thickness of passage 20a, however, is relatively large and/or the tube material is especially constructed to resist collapsing under vacuum at warmer temperatures. Since the sample conduit is made of clear material, an operator can visually observe the sample as it is being taken, which is an aid in sampling interspersed water-oil "slugs".

Line 22 is positioned through passage 20b which terminates at a point above the lower end of passage 20a. Line 22 is connected by means of safety and grounding hook 23 to eye 24 on sounding bob 21 (see FIG. 2). The flexible steel support-and-grounding line 22 assures electrical continuity between the sounding bob 21, through the conductive reel 33 to the grounding-and-clamp wire 38b (FIG. 5). This is an important safety consideration for use of the sampler in many otherwise hazardous sampling environments, e.g. inert gas and/or explosive-vapor atmospheres.

Sounding bob 21 is similar to a brass or other conventional water-sounding bobs in that it is calibrated for depth measurements but is modified (1) to accommodate conduit 20 and (2) to make the bob more portable. It may differ from other conventional water-sounding bobs in that preferably it is simultaneously calibrated on three different sides in three separate unit scales, e.g. metric divisions in millimeters; inch divisions in sixteenths; inch divisions in twentieths. Preferably, bob 21 is constructed in a plurality of sections, 21a, 21b, 21c, which are coupled together when desired. FIG. 4 illustrates a typical joint for coupling the sections together wherein projection 25 on section 21a is received by recess 26 in section 21b. A set screw 27 or the like is used to secure the two sections together. It should be understood that other known coupling means can be used to assemble the sections of bob 21 without departing from the present invention.

A groove 28 runs along the length of one edge of bob 21 and is adapted to receive and hold that portion of passage 20a of conduit 20 which extends downward from the termination point of passage 20b (see FIG. 2). Passage 20a is flexible and can be slightly compressed to "snap" it into groove 28. Bob 21 is recessed at its lowermost end 29 and passage 20a will normally terminate within this recess so that the end of passage 20a will lie or can be set to remain a short distance, e.g. ¼ inch or more as desired, above the bottom of bob 21. This positions the lower end of passage 20a at a variable point 30 (FIG. 1) above the bottom 12 of tank 11 and within water layer 15 when bob 21 rests on bottom 12.

Conduit 20 is passed over hand-held reel 33 on which the entire length of the conduit 20 is normally stored. As illustrated in FIG. 5, the upper few feet of conduit 20 extends from the main storage sheave 36 through opening 34 in divider 35 and onto small sheave 37. It can be seen that upper free end 20a of conduit 20, which can be temporarily secured in sheave 37 for storage, is readily accessible without unreeling the entire length of conduit 20. Line 22 exits conduit 20b immediately after conduit 20 has cleared divider 35 and is attached for support and grounding purposes to divider 35 at point 38a. Ground-and-clamp wire 38b attached to reel handle 38 complete the bob 21-line 22-reel 33 grounding system. As shown in FIG. 1 when sampling apparatus 10 is in an operable position, passage 20a is connected to a suction source 40 through a valve means 41. Although any suction source 40 can be used, preferably a single stroke, hand-held pump such as commercially available Models 33760 (or 33799) manufactured by Jabsco Products-ITT is used due to its portability. Likewise, while any device, e.g. pinch clamp, capable of opening and closing passage 20a can be used as valve means 41, a simple ball valve, gate valve, stock cock, etc. will suffice. All of the components of sampling apparatus 10 having now been described, the method for obtaining a liquid sample from cargo tank 11 and how it would be incorporated into a cargo oil loading operation will now be set forth.

Cargo tank 11 is loaded with cargo oil 14 and the ullage U is measured as is well understood in the art. By using standard ullage tables derived for tank 11, the total volume of liquid in tank 11 is determined. Next, the components of sampling apparatus are removed from their storage container and sections 21a, 21c are assembled to form sounding bob 21. The lower end of conduit 20 is unreeled from reel 33 and the extended portion of passage 20a is secured into groove 28 on bob 21 with the lower end of passage 20a being positioned in recess 29 at a desired height above the lower end of bob 21. Hook 23 on line 22 is secured to eye 24 on bob 21.

Pump 40 is connected to valve 41 on the upper end of passage 20a and the valve is closed to seal passage 20a. Bob 21 is coated with some water-sounding paste, e.g. Kolor-Kut, or other, which will be unaffected by dry cargo oil but will change color when contacted by water or water-oil emulsion. Conduit 20 is then unreeled to lower bob 21 to the bottom of tank 11. With the lower end of bob 21 touching bottom 12, the lower end of passage 20a will be held as set slightly above bottom 12 and be positioned in water layer 15 if such a layer is present as is determined and indicated by the observed level of color change in the water-sounding paste coating the bob 21.

Since valve 41 closes passage 20a at the top, only a trace of cargo oil, if any, will rise in passage 20a as it is lowered into position. However, with bob 21 on bottom 12, when valve 41 is open, the head of liquid in tank 11 will force liquid from layer 15 to rise in passage 20a until it is at substantially the same level as the liquid surface in tank 11. Then, a few strokes of pump 40 will draw the liquid in passage 20a the rest of the way and discharge it into a sampling container 50. Due to differences in gravity and immiscibility, any oil in the sample will rise separately in the sample container and overflow, leaving a layer of water below suitable for analysis to determine its source. Conduit 20 is reeled back onto reel 33 to retrieve bob 21 to determine by Innage measurement the volume of water in tank 11 and to assure that the open end of passage 20a still remains as initially set, i.e., within layer 15 when bob 21 rests on the bottom 12.

Although the preferred sampling apparatus has been described in detail, the method could be carried out by attaching a tubing to a standard sounding bob and then fastening the tubing at intervals to the line used to lower the bob. The tubing would be closed at the top with a valve or pinch clamp and then lowered with the bob to the bottom. The tubing would then be opened and suction applied to recover the sample in the same manner as described above.

Another embodiment of sampling apparatus 10 is shown in FIG. 6. Conduit 20 instead of being formed of siamese tubing is comprised of a single tube 20c made of the same type of plastic material as disclosed above. Conduit 20c is encased along its length from reel 33 to a point at which it is affixed to bob 21 in a snug fitting but relatively open-weave braided metallic wire sheath 55. Sheath 55 is secured on conduit 20c by upper and lower collars 56, 57, respectively. Safety hook 58 is secured to lower collar 57 for attaching conduit 20c to eye 24 on bob 21. Sheath 55 provides both support and grounding for conduit 20c during sampling operations.

Further, if it is desirable to obtain samples from more than one level within a liquid container, then multiple conduits, each terminating at a different level above the bob and each being controlled by a separate valve, can be affixed together and lowered with the sounding bob. The conduits can be color-coded to aid in identifying which sample is taken from what level.

As mentioned above, normally a trace of cargo oil in sample passage 20a of FIG. 1 or conduit 20c of FIG. 6 will not create any problems in the sampling operations. However, in those loading situations where the cargo oil has a low vapor pressure and/or where temperatures are high, a trace of cargo oil may flash or vaporize as it rises in the sample passage 20a ahead of the desired sample. This vaporized oil will usually cause "vapor lock" problems for suction source 41 which are annoying and time-consuming to overcome.

To alleviate such problems, sampling apparatus 10 is modified by providing an upward opening check valve 60 (see FIGS. 7 and 8) in the lower end of sample passage 20a (FIG. 1) or conduit 20c (FIG. 6). Passage 20a or conduit 20c is then filled with a nonvaporizing and preferably oil-and-water immiscible liquid (e.g. fluorinated kerosine, or at least pure or distilled water, or the like) drawn from a supply container (not shown) and valve 41 (FIG. 1) is closed to trap the nonvaporizing liquid or pure water in sample passage 20a or conduit 20c to prevent check valve 60 from opening as the conduit is lowered into tank 11. When bob 21 is in place to sample on the tank bottom, valve 41 is reopened and suction means 40 is again actuated. Valve 61 in check valve 60 can now move up against stops 62 thereby opening valve 60 to allow the sample to flow upward in passage 20a or conduit 20c behind the immiscible liquid for recovery.

To simplify the immediately above described operation, valve 41 is a multiposition valve, e.g. the valve shown in FIGS. 9, 10 and 11. Valve 41, as illustrated, is a spool valve having a housing 65 which has four inlets 66, 67, 68, 69 and opening 70 normally open to the atmosphere. To sample or to fill passage 20a or conduit 20c with immiscible liquid, as shown in FIG. 10 inlet 66 is in fluid communication with sample passage 20a or conduit 20c, inlet 67 is in fluid communication with sample container 50, inlet 68 is in fluid communication with the suction inlet of pump 40, and inlet 69 is in fluid communication with the discharge outlet at pump 40. Spool 71 has a 2-outlet passage 72 (see FIGS. 10, 11) therethrough which lies in the same radial plane as do inlets 66, 68, and 70 and a 2-outlet passage 73 which normally communicates inlets 69 and 67 when passage 72 communicates inlets 66 and 68. Passage 73 also has a longitudinal offset portion 74 which can in another position communicate the radial plane of inlet 69 to the radial plan of inlet 66 when passage 72 communicates inlet 68 with air inlet 70. A handle 75 is attached to spool 71 by which spool 71 can be rotated to its various positions.

With valve 41 in the position shown in FIG. 10, the nonvaporizing liquid is supplied to inlet 66 via passage 20a or conduit 20c from a supply container (not shown). In this position when pump 40 is actuated the immiscible liquid will be drawn through passage 20a or conduit 20c via inlet 66 into inlet 68, pump 40, inlet 69, passage 73, and out inlet 67 to fill the sample system, i.e., passage 20a or conduit 20c. When filled, spool 71 of valve 41 is moved to an intermediate position (not shown) to trap this immiscible liquid in sample passage 20a or conduit 20c. Conduit 20 is then lowered to an operable position in the tank as described in the first embodiment. Spool 71 of valve 41 is then moved back into the position shown in FIG. 10 and pump 40 is again actuated. The immiscible liquid originally placed in sample passage 20a or conduit 20c followed by the desired sample will be drawn up sample passage 20a or conduit 20c through valve 41 and pump 40 and out through inlet 67 to be preferentially discharged into sample container 50. After the desired sample has been recovered, valve 41 is again closed and conduit 20 is reeled in on reel 33 and check valve 60 is removed from the end of passage 20a. Spool 71 is now moved to the position shown in FIG. 11 and now by actuating pump 40, air will be drawn through opening 70 into valve 41 and will be forced into passage 20a via valve passages 73 and 74 to thereby purge the remaining liquid from passage 20a. This latter step of purging the sample passage can also be used equally as well in the embodiment of FIGS. 1 and 6.

From the above description, it can be seen that the present invention provides an inexpensive, safe, reliable method and self-contained apparatus for obtaining a sample of liquid from near the bottom of a liquid-filled container. The apparatus is portable and easily storable when not in use which makes it the type of apparatus which can be easily carried aboard all tankers having a need therefor.

What is claimed:

1. A method for obtaining a sample of liquid from a selected depth very near the bottom of a cargo tank substantially filled with cargo oil, said method comprising:
   attaching a flexible conduit to a water-sounding bob;
   closing said flexible conduit at its upper end;
   lowering said flexible conduit with said bob to a selected point adjacent the bottom of said tank;
   electrically grounding said bob while it is in said tank;
   opening said flexible conduit at its upper end to permit liquid from near the bottom of said tank to flow upward in said flexible conduit to a level substantially equal to the surface level of liquid in said tank;
   applying suction to said upper end of said flexible conduit to recover said sample; and
   purging said flexible conduit after the sample has been recovered.

2. An apparatus for obtaining a liquid sample from any selected depth in a liquid-filled tank, comprising:
   a bob adapted to be lowered into said tank;
   a line attached to said bob for raising and lowering said bob in said tank;
   means for electrically grounding said line and bob during said raising and lowering;
   a flexible conduit attached to said bob and adapted to be lowered and raised therewith in said tank;
   valve means for opening and closing the upper end of said flexible conduit; and
   means for applying suction to said upper end of said flexible conduit.

3. The apparatus of claim 2 wherein said means for applying suction comprises:
   a hand-held pump.

4. The apparatus of claim 2 including:
   a reel for lowering and raising said flexible conduit and said line in said tank.

5. The apparatus of claim 2 including:
   an upward-opening check valve positioned in the lower end of said flexible conduit.

6. The apparatus of claim 2 wherein said flexible conduit comprises:
   a siamese tube forming a first passage and a second passage, said line passing through said first passage and said second passage providing the passage through which the sample is to be recovered.

7. An apparatus for obtaining a sample from a water and/or water-oil emulsion layer underlying cargo oil in a cargo tank, said apparatus comprising:
   a water-sounding bob for determining the presence of water in said cargo tank;
   a support means attached to said water-sounding bob for lowering and raising said bob in said tank;
   a flexible conduit attached at its lower end to said bob and along its intermediate length to said support means, said lower end of said flexible conduit is attached at a point above the bottom of said bob so that when said bob rests on the bottom of said tank, said lower end of said flexible conduit will be held at a selected point above the bottom of said tank;
   a valve means associated with the upper end of said flexible conduit for opening and closing said conduit; and
   means for applying suction to said upper end of said flexible conduit.

8. The apparatus of claim 7 wherein said flexible support means comprises:
   a flexible metallic sheath encasing said conduit.

9. The apparatus of claim 7 wherein said support means comprises:
   a metallic line and wherein said apparatus includes:
   means for electrically grounding said line and said bob.

10. The apparatus of claim 9 including:
    a reel for lowering and raising said flexible conduit and said line in said tank.

11. The apparatus of claim 10 including:
    means for purging said flexible conduit.

12. The apparatus of claim 11 wherein said means for applying suction and for purging said flexible conduit comprises:
    a hand-held pump.

13. The apparatus of claim 12 including:
    an upward-opening check valve in the lower end of said flexible conduit.

14. The apparatus of claim 13 wherein said flexible conduit is comprised of a clear, flexible material and is constructed to form two separate passages, one of said passages providing the passage through which the sample is obtained and the other of said passages having said line passed therethrough.

* * * * *